US00PP28226P3

(12) United States Plant Patent
Olesen

(10) Patent No.: US PP28,226 P3
(45) Date of Patent: Aug. 1, 2017

(54) COMPACT FLORIBUNDA ROSE PLANT NAMED 'POULPAL061'

(50) Latin Name: ***Rosa* hybrid**
Varietal Denomination: Poulpal061

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 14/756,269

(22) Filed: Aug. 20, 2015

(65) Prior Publication Data

US 2017/0055399 P1 Feb. 23, 2017

(51) Int. Cl.
*A01H 5/02* (2006.01)

(52) U.S. Cl.
USPC ..... Plt./143

(58) Field of Classification Search
USPC ..... Plt./143
See application file for complete search history.

(56) References Cited

PUBLICATIONS

Poulsen Roser A/S "Palace-Perfection by Poulsen" Oct. 2012 (1 page).*

* cited by examiner

*Primary Examiner* — Susan McCormick Ewoldt

(57) ABSTRACT

A new garden rose plant of the Compact Floribunda class which has abundant, orange red flowers with yellow stripes and attractive foliage. This new and distinct variety has shown to be uniform and stable in the resulting generations from asexual propagation.

2 Drawing Sheets

Botanical designation: *Rosa* hybrid.
Variety denomination: 'Poulpal061'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2005 and the resulting seeds were planted in a controlled environment in Fredensborg, Denmark. The new variety, named 'Poulpal061', originated as a single seedling from the stated cross.

The new variety may be distinguished from its male pollen parent and female seed parent primarily by the following characteristics. The male pollen parent has apricot blend flowers while the new variety has orange red flowers with yellow stripes. The female seed parent has red flowers while the new variety has orange red flowers with yellow stripes.

The objective of the hybridization of this rose variety was to create a new and distinct variety for garden use with unique qualities, such as:

1. Uniform and abundant orange red flowers with yellow stripes;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal061' from all other varieties of which we are aware.

As part of the rose development program, Mogens N. Olesen germinated the seeds from the aforementioned hybridization during winter of 2005 and conducted evaluations on the resulting seedlings in a controlled environment in Fredensborg, Denmark. 'Poulpal061' was selected in the spring of 2006 by the inventor as a single plant from the progeny of the aforementioned hybridization.

Asexual reproduction of 'Poulpal061' by traditional budding and rooted cuttings was first done by Mogens N. Olesen in the nursery in Fredensborg, Denmark in July, 2006. This initial and other subsequent asexual propagations conducted in controlled environments have demonstrated that the characteristics of 'Poulpal061' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal061'.

Specifically illustrated in FIG. 1 of the drawings is a cluster of open flowers, flower petals detached, sepals detached, and reproductive flower parts.

Figure 1:
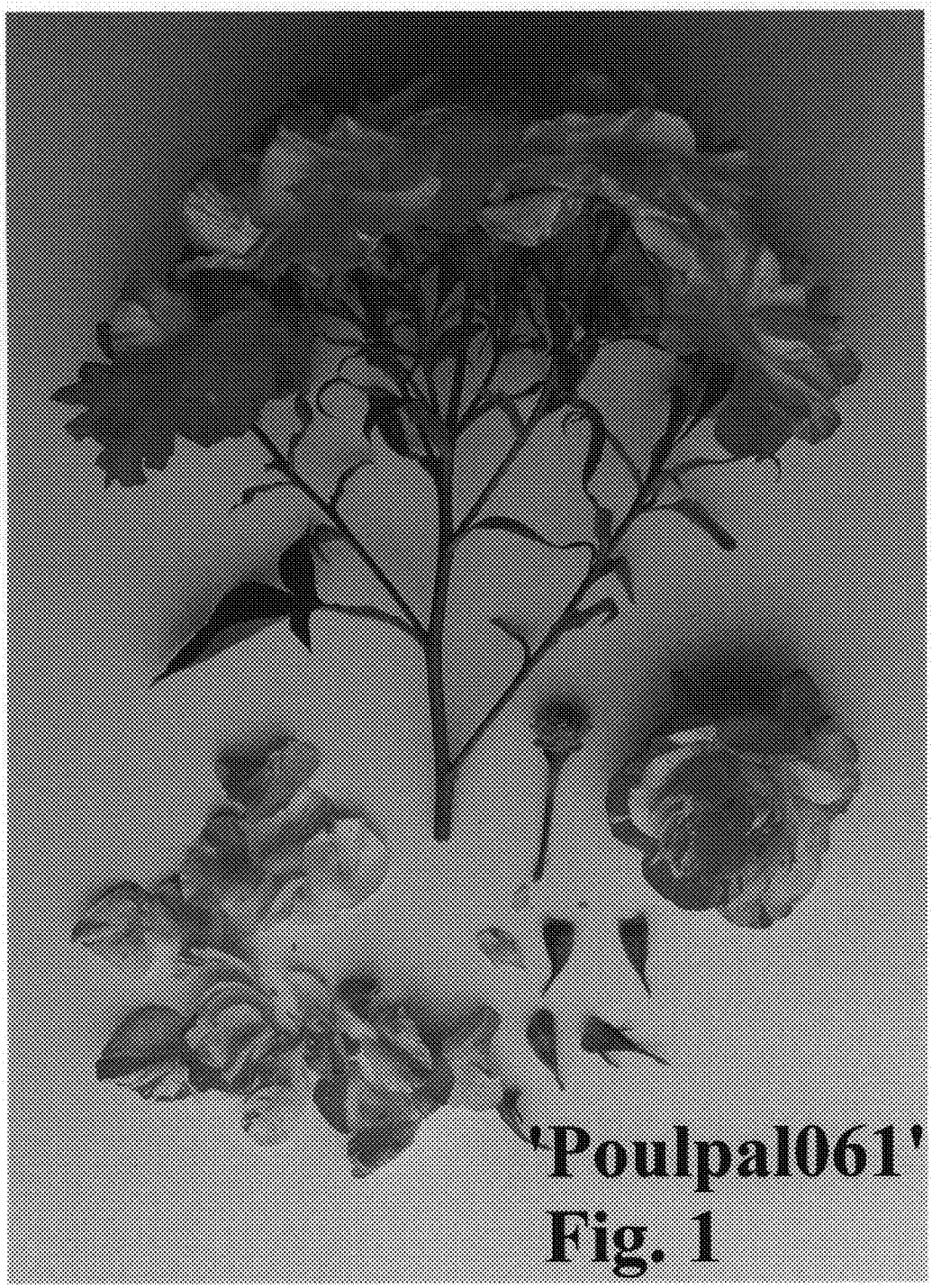
Figure 2:
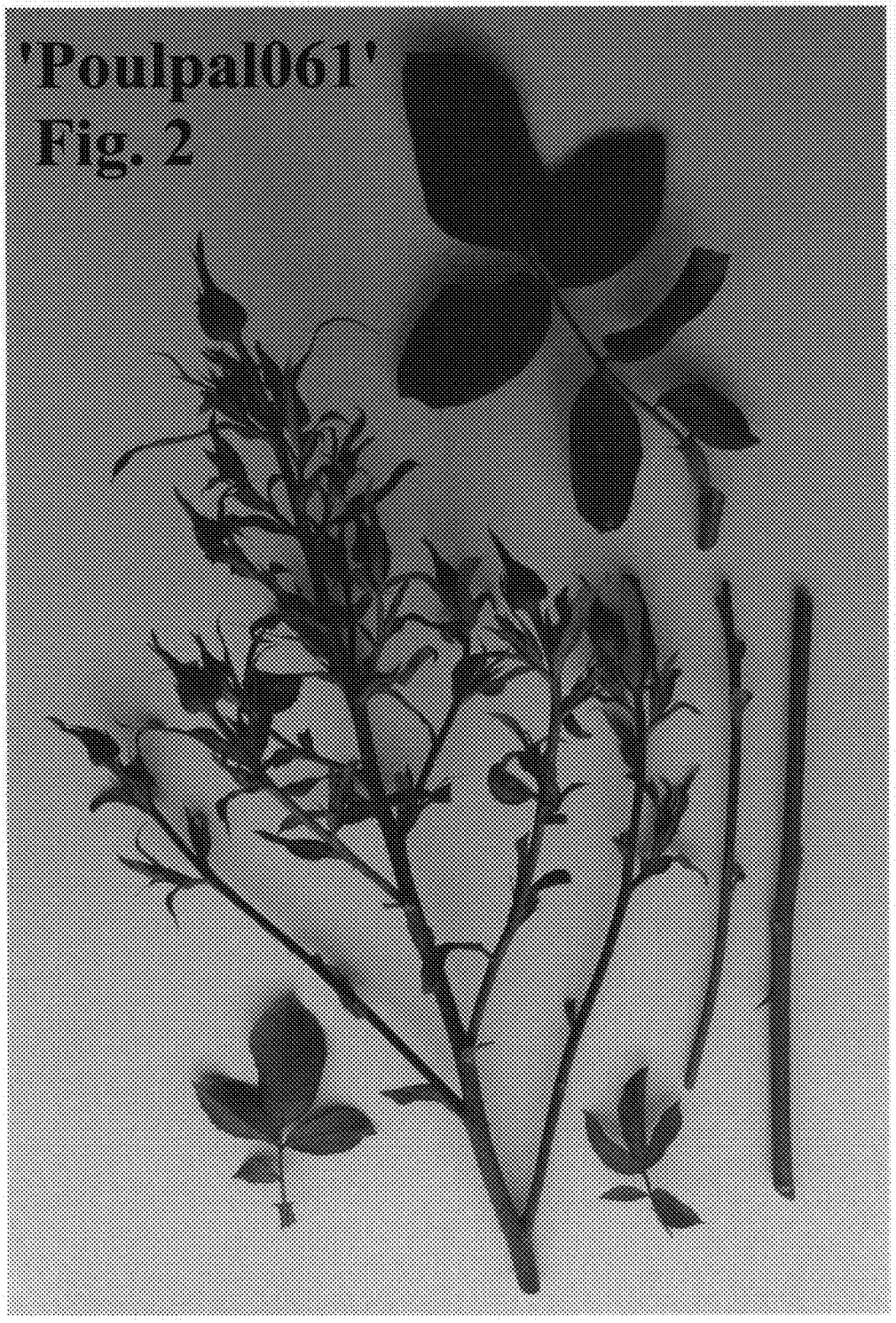

Specifically illustrated in FIG. 2 of the drawings is a flowering branch showing flower buds and peduncles, juvenile leaves, mature leaves, and bare stems. Plants shown are 2 years of age.

DETAILED DESCRIPTION OF THE VARIETY

The following is a description of 'Poulpal061', as observed in its growth in in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah024', U.S. Plant Pat. No. 18,729 are compared to 'Poulpal061' in Chart 1.

CHART 1

| | 'Poulpal061' | 'Poulpah024' |
|---|---|---|
| Petal Count | 35 | 90 |
| Flower Diameter | 75 mm | 55 to 60 mm |
| Upper surface of outer petals after opening | Red Group 43A at marginal zone. Red Group 41B at middle zone. Splashed with White Group 155C | Red-Purple Group 57A to 58B with streaks of White Group 155B and or Yellow Group 5D layered over |

FLOWER AND FLOWER BUD

Blooming habit: Continuous.

Flower bud:

*Size*.—Upon opening, 28 mm in length from base of receptacle to end of bud. Bud diameter is 16 mm.

*Bud form*.—Ovoid.

*Bud color*.—As sepals divide petals are Red Group 40C and Yellow Group 10B.

*Sepal inner surface*.—Color: Yellow-Green Group 147D. Surface: Lightly pubescent.

*Sepal outer surface*.—Color: Yellow-Green Group 144A with moderate intonations of Greyed-Orange Group 175A. Texture: Somewhat rough.

*Sepal shape*.—Apex: Cirrhose. Base: Flat at union with receptacle.

*Sepal margin*.—Margins have weak foliaceous appendages on three of the five sepals.

*Sepal size*.—20 mm long, 10 mm wide.

*Receptacle*.—Texture: Smooth. Size: 6 mm in height, 7 mm wide. Color: Yellow-Green Group 144A with intonations of Greyed-Orange Group 166A. Shape: Campanulate.

*Pedicel*.—Surface: Rough. Length: 25 to 30 mm. Diameter: 2 mm on average. Color: Yellow-Green Group 144A with intonations of Greyed-Purple Group 184A. Strength: Strong.

*Peduncle*.—Length: 4 to 11 cm. Diameter: About 3 mm. Color: Yellow-Green Group 145A with intonations of Greyed-Purple Group 184A. Texture: Smooth.

Flower bud development: Flower buds are borne in corymbs of 12 to 15 buds per stem. Corymbs are about 15 cm in diameter.

Flower bloom:

*Fragrance*.—Moderate floral.

*Duration*.—The blooms have a duration on the plant of approximately 14 days. Petals fall cleanly away from plant after flowers have fully matured.

*Size*.—Flower diameter is 75 mm when open. Flower depth is 35 mm.

*Flower shape*.—Open cup double flower, with petals that curve out from the center.

*Shape of flower, side view*.—The upper portion is flattened convex. The lower portion is concave.

Petalage: Under normal conditions, flowers have 35 petals total, 5 of which are petaloids.

General tonality of flower: Open flowers are Red Group 40A and Yellow Group 10A.

Petal color:

*Upon opening, outer & inner petals*.—Upper surface: Splashed with Orange-Red Group 33A and Red Group 38B. At the basal zone Yellow Group 10A. Lower surface: Red Group 43C splashed with White Group 155C and Yellow Group 4D.

*Basal petal spots, upon opening*.—Upper surface: Yellow Group 10A. Lower surface: Yellow Group 10C.

*After opening, outer and inner petals*.—Upper surface: Red Group 43A at marginal zone. Red Group 41B at middle zone. Splashed with White Group 155C Lower surface: Red Group 52C splashed with White Group 155C and Yellow Group 4D.

*Basal petal spots, after opening*.—Upper surface: Yellow Group 10A. Lower surface: Yellow Group 10C.

Petals:

*Petal reflex*.—Moderately reflexed.

*Margin*.—Entire and uniform. Strong undulations.

*Shape*.—Generally elliptical. Apex shape: Rounded. Base shape: Acute.

*Size*.—35 mm (l)×35 mm (w).

*Texture*.—Smooth.

*Thickness*.—Average.

Petaloids:

*Size*.—17 mm (l) by 11 mm (w).

*Quantity*.—About 5.

*Shape*.—Crescent shaped.

*Color*.—Upper surface is Orange-Red Group N30A and Yellow Group 9A. The lower surface is Red Group 41C and Yellow Group 4A.

Reproductive flower parts:

*Pollen*.—None observed.

*Anthers*.—Size: 2 mm in length. Color: Yellow Group 10C. Quantity: 50 on average.

*Filaments*.—Color: Yellow Group 7B. Length: 5 mm.

*Pistils*.—Length: 10 mm. Quantity: 30 on average.

*Stigmas*.—Color: Greyed-Yellow Group 162B.

*Styles*.—Color: Green-White Group 157A.

*Location of stigmas*.—Level in location relative to the length of the filaments and the height of the anthers.

*Hips*.—None observed to date.

PLANT

Plant growth: Upright, bushy. Plants are 80 cm in height, and 70 cm wide.

Stems:

*Color*.—Juvenile growth: Yellow-Green Group 144B and Greyed-Red Group 181A. Mature growth: Yellow-Green Group 144A.

*Length*.—On average, canes are 40 cm from the base of the plant to the flowering portion.

*Diameter*.—5 mm.

*Internodes*.—On mature canes about 65 mm between nodes.

*Surface texture*.—Young wood: Rough. Older wood: Smooth.

Long prickles:

*Incidence*.—2 prickles per 10 cm of stem.

*Size*.—Average length of prickles on mature stems is 4 mm.

*Shape*.—Upper portion is linear. Lower portion is concave.

*Color*.—Juvenile prickles: Greyed-Red Group 179A. Mature prickles: Greyed-Red Group 179B.

Plant foliage:

*Compound leaf*.—120 mm (l)×110 (w).

*Quantity*.—2 leaves per 10 cm of stem on average.

*Color of juvenile foliage*.—Upper side: Yellow-Green Group 146B. Lower side: Yellow-Green Group 146B. Anthocyanin: Greyed-Purple Group 183B.

*Color of mature foliage*.—Upper side: Yellow-Green Group 146A. Lower side: Yellow-Green Group 146B.

Plant leaves and leaflets:

*Stipules*.—Size: 30 mm long, 13 mm wide. Quantity: 2 per compound leaf. Shape: Linear, slightly broad based with outward extending apices. Margins: Finely serrated. Color: Yellow-Green Group 144A.

*Petiole*.—Length: 40 mm. Diameter: 1.5 mm.

*Upper surface*.—Color: Yellow-Green Group 144A.

*Lower surface*.—Color: Yellow-Green Group 144A.

*Rachis*.—Length: 45 mm. Upper surface: Color: Yellow-Green Group 144A.

*Lower surface*.—Color: Yellow-Green Group 144A.

*Leaflet*.—Quantity: Normally 5 leaflets. Margins: Serrated. Size: On average terminal leaflets are 75 mm long, 40 mm wide. Shape: Generally elliptical. Base: Rounded. Apex: Mucronate. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal061', substantially as illustrated and described herein, due to its abundant orange red flowers with yellow stripes, disease resistance, and extended period of bloom.

* * * * *

'Poulpal061'

'Poulpal061'